United States Patent
Huffmaster

(10) Patent No.: US 7,998,165 B2
(45) Date of Patent: *Aug. 16, 2011

(54) LASER-CUT CLOT PULLER

(75) Inventor: Andrew Huffmaster, Fremont, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 769 days.

This patent is subject to a terminal disclaimer.

(21) Appl. No.: 11/946,106

(22) Filed: Nov. 28, 2007

(65) Prior Publication Data

US 2008/0119888 A1    May 22, 2008

Related U.S. Application Data

(63) Continuation of application No. 10/639,705, filed on Aug. 12, 2003, now Pat. No. 7,316,692.

(51) Int. Cl.
*A61M 29/00* (2006.01)

(52) U.S. Cl. .................. 606/200; 604/104

(58) Field of Classification Search ............. 606/113, 606/127, 200, 108, 159, 198; 623/1.11, 1.12, 623/1.15; 604/104

See application file for complete search history.

(56) References Cited

U.S. PATENT DOCUMENTS

| | | | |
|---|---|---|---|
| 4,425,908 A | 1/1984 | Simon | |
| 5,108,419 A * | 4/1992 | Reger et al. | 606/200 |
| 5,192,286 A | 3/1993 | Phan et al. | |
| 5,669,933 A | 9/1997 | Simon et al. | |
| 5,709,704 A | 1/1998 | Nott et al. | |
| 5,772,609 A | 6/1998 | Nguyen et al. | |
| 5,836,968 A | 11/1998 | Simon et al. | |
| 5,941,896 A | 8/1999 | Kerr | |
| 6,001,118 A | 12/1999 | Daniel et al. | |
| 6,007,558 A | 12/1999 | Ravenscroft et al. | |
| 6,013,093 A | 1/2000 | Nott et al. | |
| 6,139,510 A | 10/2000 | Palermo | |
| 6,152,946 A | 11/2000 | Broome et al. | |
| 6,171,328 B1 | 1/2001 | Addis | |
| 6,245,012 B1 | 6/2001 | Kleshinski | |
| 6,258,026 B1 | 7/2001 | Ravenscroft et al. | |
| 6,273,900 B1 | 8/2001 | Nott et al. | |
| 6,277,139 B1 | 8/2001 | Levinson et al. | |
| 6,336,934 B1 | 1/2002 | Gilson et al. | |
| 6,383,206 B1 | 5/2002 | Gillick et al. | |
| 6,391,044 B1 * | 5/2002 | Yadav et al. | 606/200 |
| 6,436,121 B1 | 8/2002 | Blom | |
| 6,443,972 B1 | 9/2002 | Bosma et al. | |
| 6,530,939 B1 | 3/2003 | Hopkins et al. | |
| 6,551,327 B1 | 4/2003 | Dhindsa | |
| 6,551,342 B1 | 4/2003 | Shen et al. | |
| 6,562,058 B2 | 5/2003 | Seguin et al. | |
| 6,596,011 B2 | 7/2003 | Johnson et al. | |
| 7,316,692 B2 * | 1/2008 | Huffmaster | 606/127 |

FOREIGN PATENT DOCUMENTS

EP    1273268 A1    1/2003

* cited by examiner

*Primary Examiner* — Michael J Milano
*Assistant Examiner* — Victor X Nguyen
(74) *Attorney, Agent, or Firm* — Vista IP Law Group LLP

(57) ABSTRACT

A device for removing blood clots and methods of making and using the same. The clot pulling device may include a first spine, a second spine disposed parallel to the first spine, and a basket disposed between and coupled to the spines. In addition, a pushing member may be coupled to the first spine and extend proximally therefrom.

3 Claims, 5 Drawing Sheets

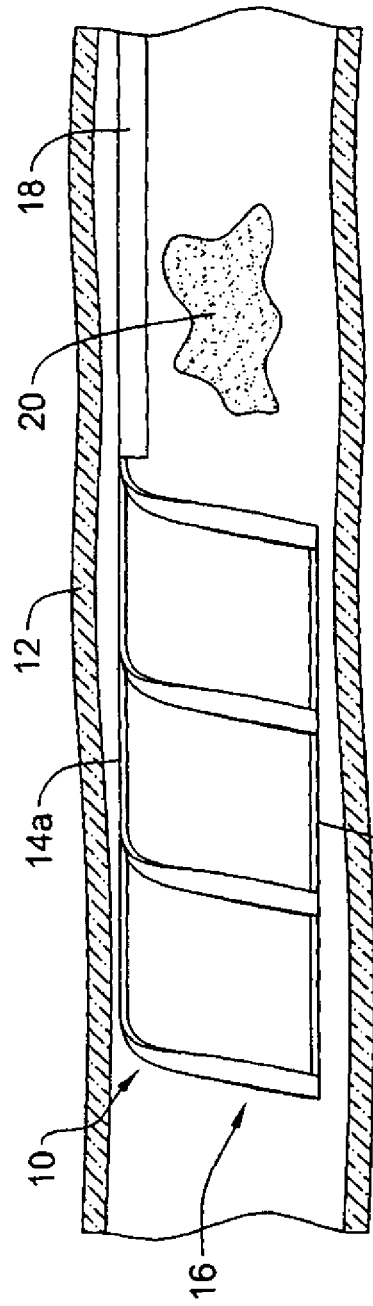
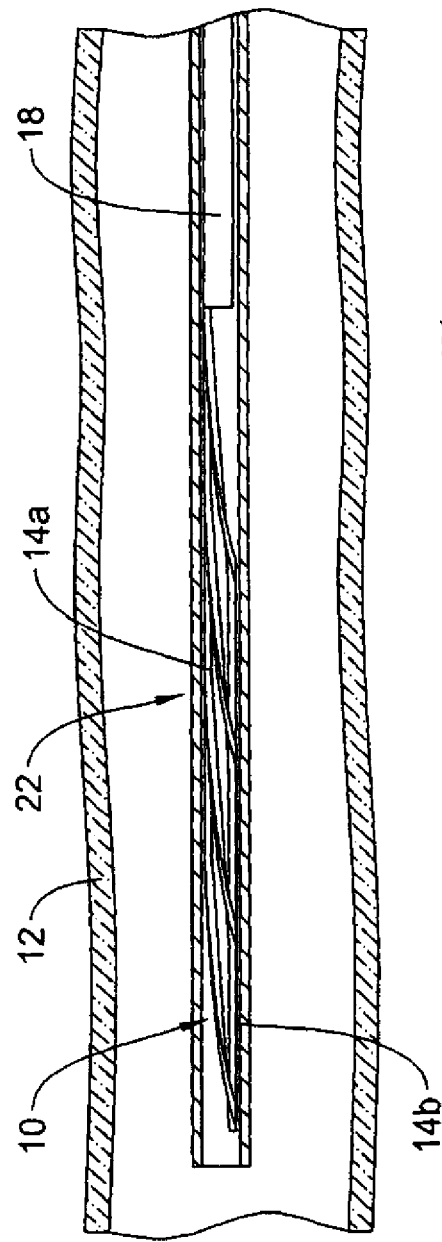

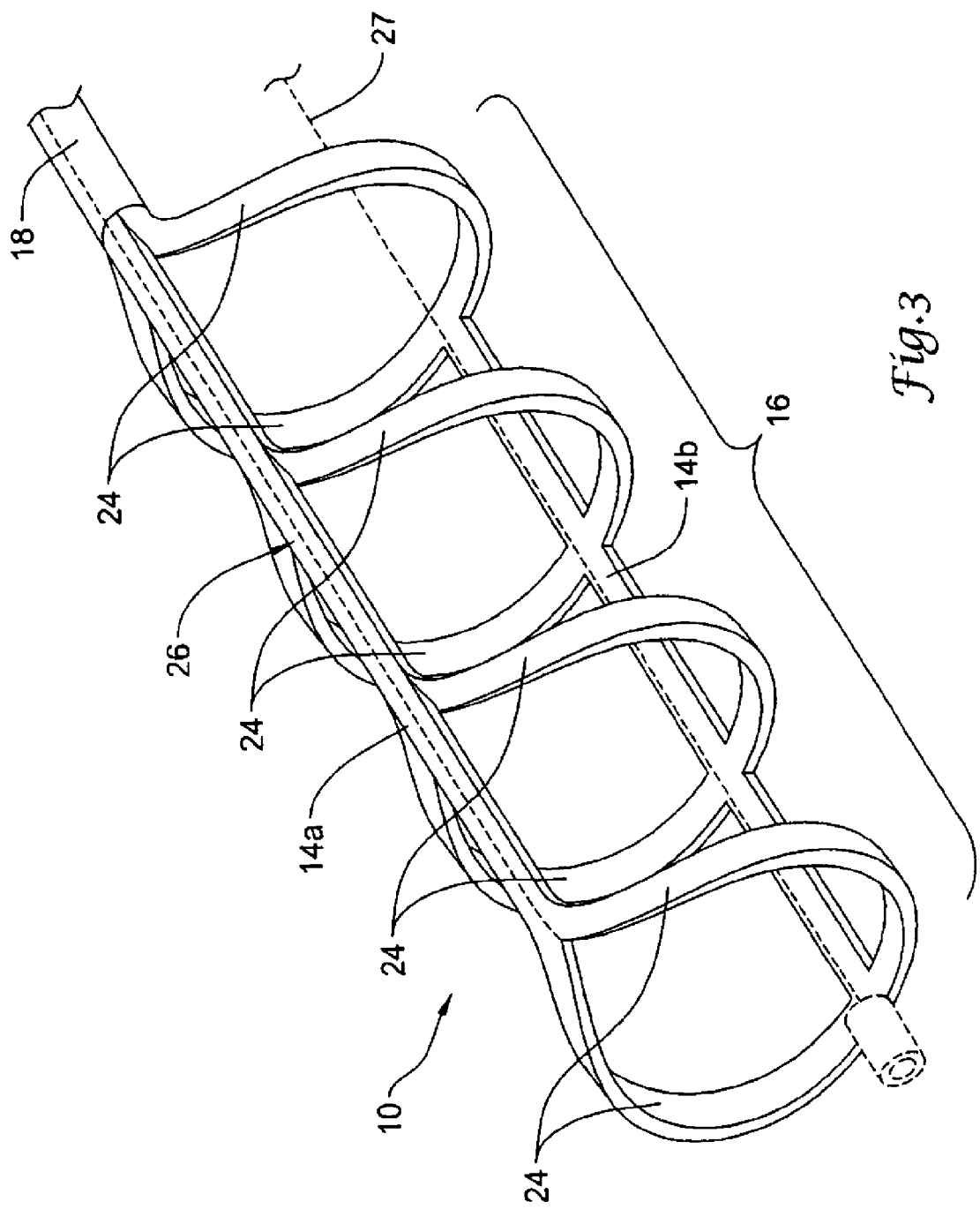

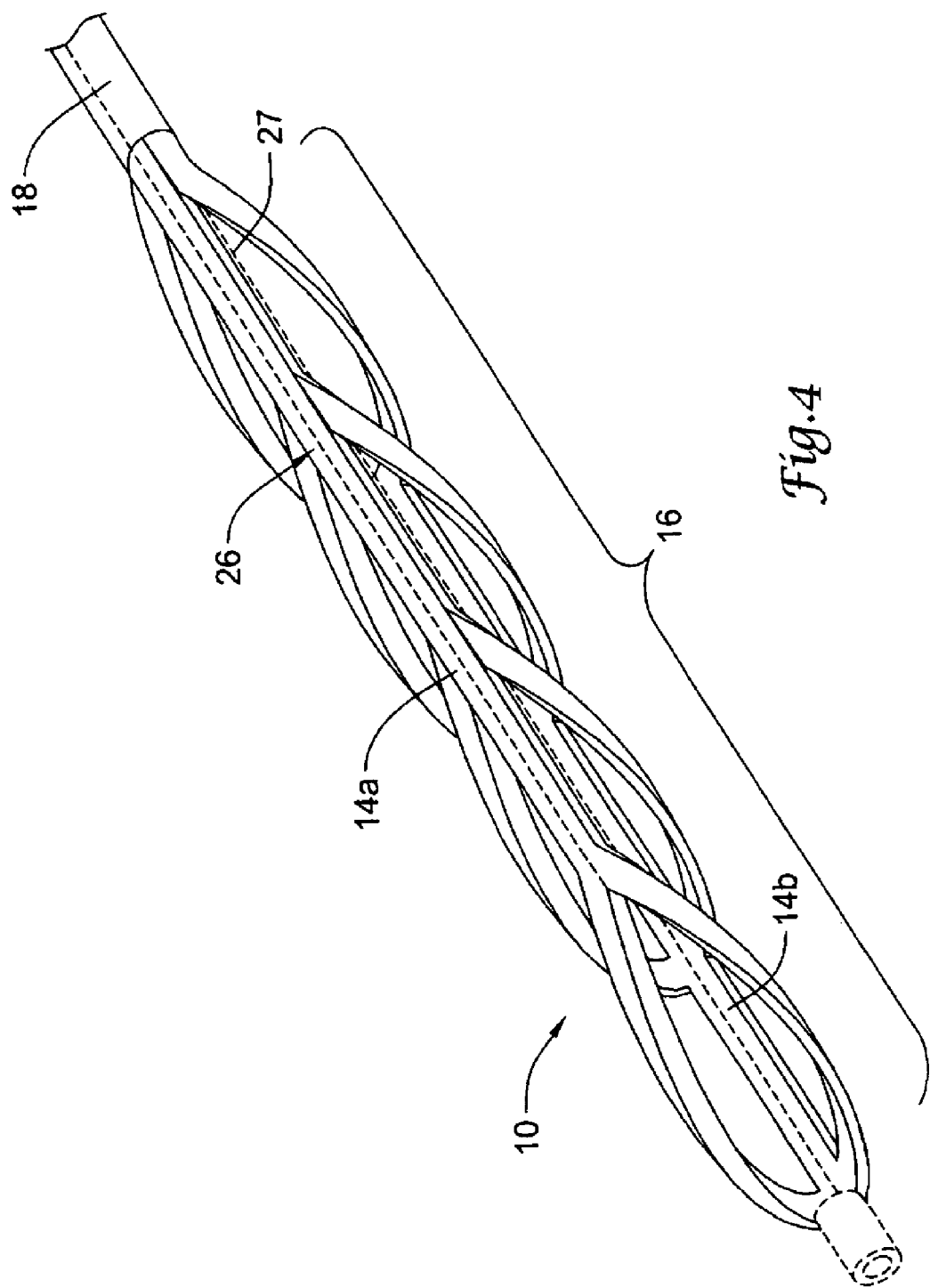

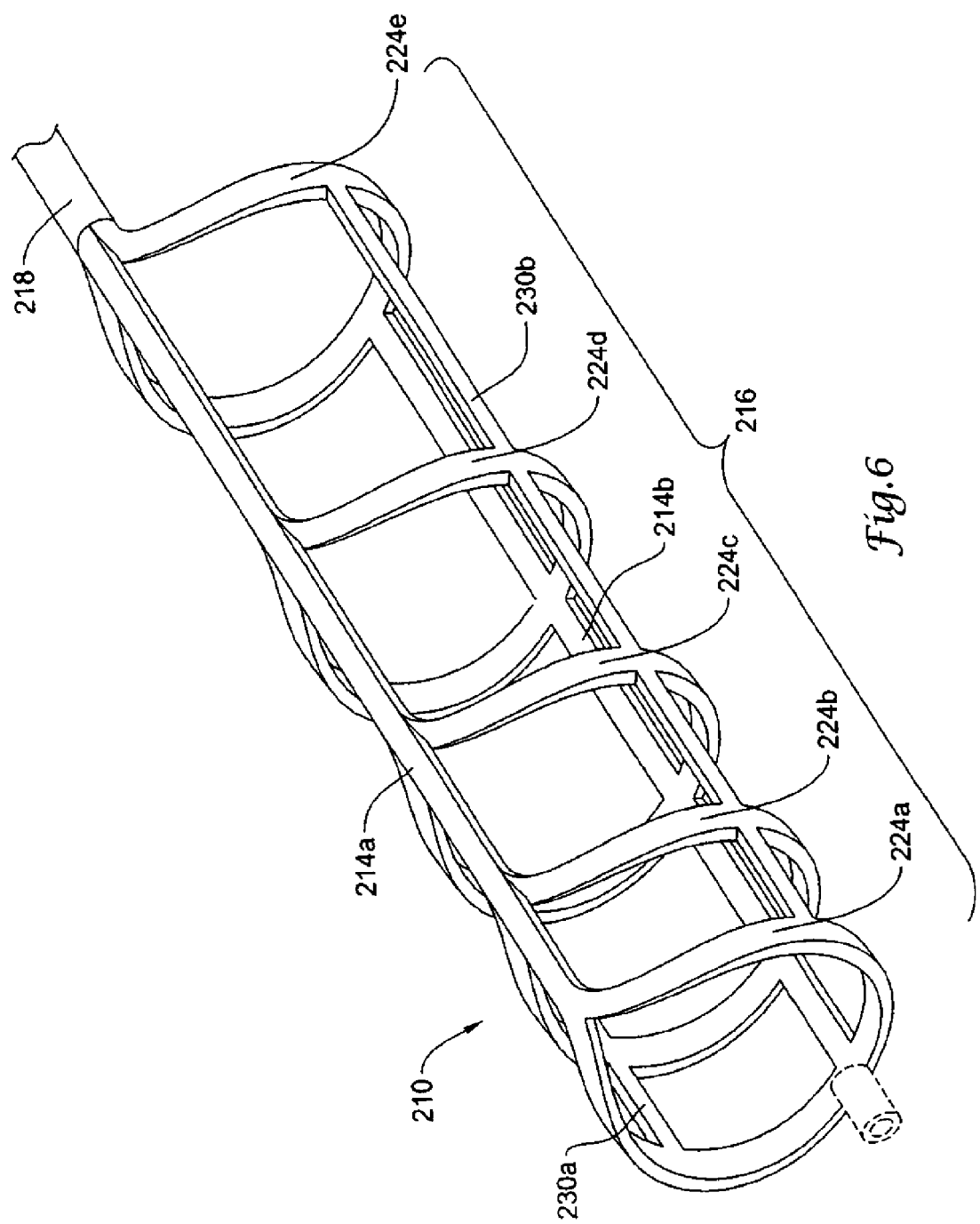

LASER-CUT CLOT PULLER

RELATED APPLICATIONS

This application is a continuation application of U.S. application Ser. No. 10/639,705 filed Aug. 12, 2003, now U.S. Pat. No. 7,316,692.

FIELD OF THE INVENTION

The present invention pertains to intravascular medical devices. More particularly, the present invention pertains to devices for capturing and removing blood clots from a blood vessel.

BACKGROUND

The present invention pertains generally to emboli collection and removal.

Blood thrombus, may form a clot in a patient vasculature. Sometimes such clots are harmlessly dissolved in the blood stream. At other times, however, such clots may lodge in a blood vessel where they can partially or completely occlude the flow of blood. If the partially or completely occluded vessel feeds blood to sensitive tissue such as, the brain, lungs or heart, for example, serious tissue damage may result.

When symptoms of an occlusion are apparent, such as an occlusion resulting in a stroke, immediate action should be taken to reduce or eliminate resultant tissue damage. One approach is to treat a patient with clot dissolving drugs. These drugs, however, do not immediately dissolve the clot from the patient.

BRIEF SUMMARY

The present invention pertains to devices for removing blood clots from blood vessels. In at least some embodiments, a clot pulling device includes a first spine, a second spine disposed generally parallel to the first spine, and a basket disposed between and coupled to the spines. A pushing member may be coupled to the first spine and extend proximally therefrom. These and some of the other structural features and characteristics are described in more detail below.

BRIEF DESCRIPTION OF THE DRAWINGS

FIG. 1 is a partial cross-sectional side view of an example medical device disposed in a blood vessel;

FIG. 2 is a partial cross-sectional side view of an example medical device disposed in a sheath within a blood vessel;

FIG. 3 is a perspective view of an example medical device;

FIG. 4 is a perspective view of the device in FIG. 3 in a collapsed configuration;

FIG. 6 is a perspective view of another example medical device.

DETAILED DESCRIPTION

Figure 5:
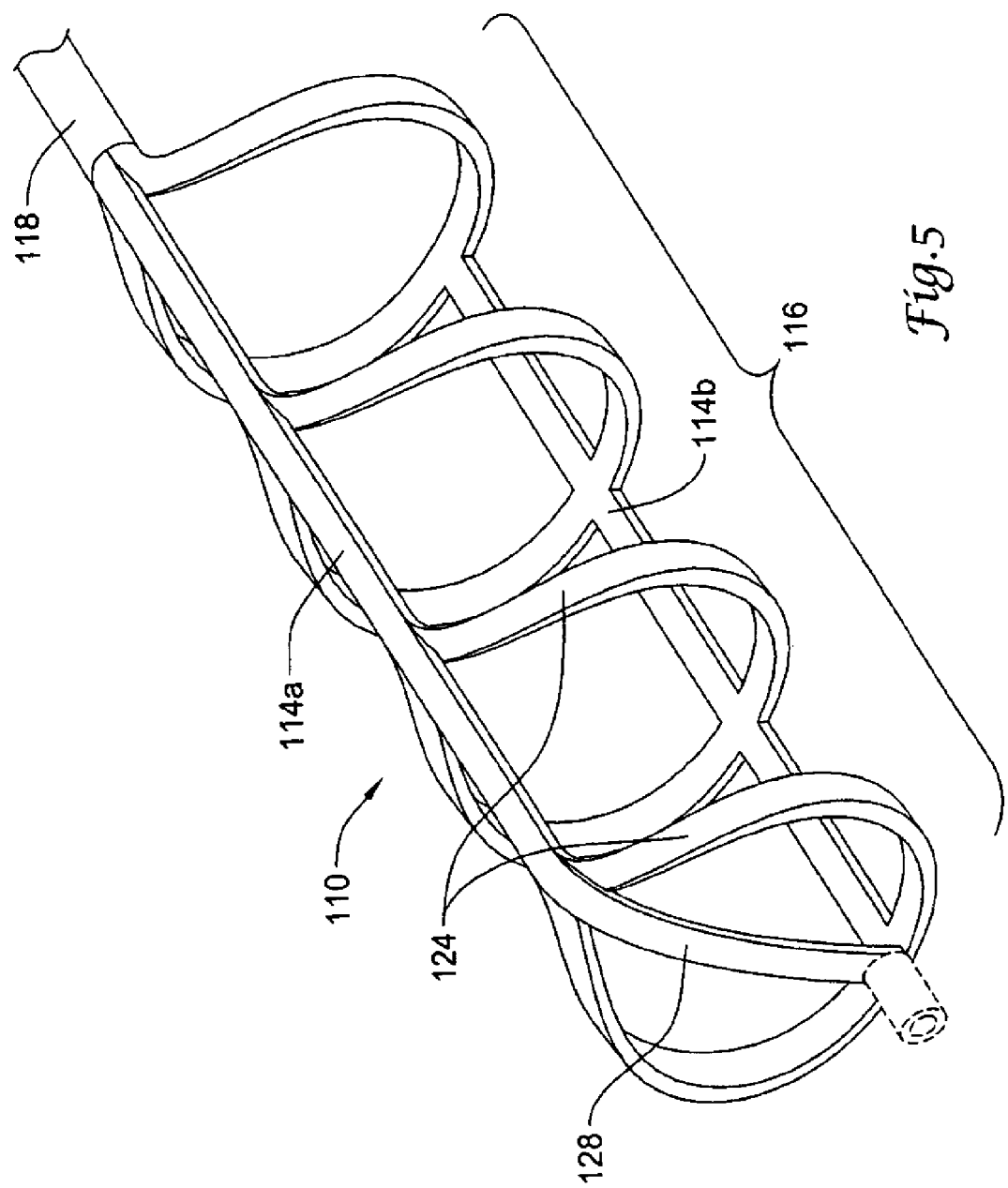
FIG. 5 is a perspective view of another example medical device.

The following description should be read with reference to the drawings wherein like reference numerals indicate like elements throughout the several views. The detailed description and drawings illustrate example embodiments of the claimed invention.

For a number of reasons, it may be desirable to capture and/or remove clots from the vasculature. FIG. 1 is a partial cross-sectional side view of an example clot pulling medical device 10 disposed in a blood vessel 12. Blood vessel 12 can be essentially any vessel. Device 10 may include two or more longitudinal spines, for example spines 14a and 14b, a basket member or region 16 that is attached to or otherwise coupled with spines 14a/b, and a proximally-extending shaft or pushing member 18. In general, device 10 can be advanced through the vasculature to a suitable location, for example adjacent a clot 20, and expanded so that clot 20 can be captured in basket region 16. Device 10 and the captured clot 20 can be removed from the vasculature.

Device 10 and/or basket region 16 may be configured to shift between a first generally collapsed configuration and a second generally expanded configuration. In at least some embodiments, shifting between these configurations includes the longitudinal movement of one or both of spines 14a/b relative to one another. Movement of spines 14a/b may occur in either the proximal or distal direction and, in the case of both spines 14a/b moving, may be in the same or opposite directions. For example, shifting may include the proximal or distal movement of spine 14b relative to spine 14a. Shifting may also result in one or both of spines 14a/b moving somewhat laterally so that spines 14a/b become closer to one another. This is because basket region 16 may be in the expanded configuration when spines 14a/b are generally aligned longitudinally and disposed parallel to one another and, when basket region 16 is collapsed, spines 14a/b longitudinally move and move closer to one another to allow basket region 16 to collapse to a lower profile (please see FIG. 2). It can be appreciated that longitudinally moving spine 14b and moving spines 14a/b closer to one another may elongate device 10, for example at basket region 16. Again, this may be due to the fact that shifting the position of spines 14a/b allows the basket region 16 to shift between the expanded and collapsed configuration. Thus, collapsing basket region 16 may generally result in the elongation of device 10.

Shifting between the collapsed and expanded configurations may occur in a number of differing manners. For example, device 10 or portions thereof may be made of a shape-memory material (such as nickel-titanium alloy) that can assume a pre-defined shape when unconstrained or when subjected to particular thermal conditions. According to this embodiment, device 10 can be manufactured to be "self-expanding" so that it can be delivered in a collapsed configuration then shift to the expanded configuration when a constraint is removed (e.g., a delivery sheath) or when device 10 is subject to the thermal conditions within blood vessel 12. Alternatively, shifting may occur by mechanically moving one or both of spines 14a/b. Moving spines 14a/b may occur in a number of different ways such as by moving shaft 18 or another shaft (for example shaft 27 as shown in FIG. 3) that may be, for example, attached to the distal end of device 10 and/or spine 14b.

Spines 14a/b may generally be connected to the proximal and distal ends of basket region 16, respectively, and be manufactured or otherwise configured to be moved independently of one another. This may allow basket region 16 to be easily collapsed by shifting the position of spines 14a/b. Additionally, because the collapsing of device 10 and/or basket region 16 includes the longitudinal shifting of spines 14a/b, outward radial forces are reduced. This may allow device 10 to more easily be disposed in or otherwise advance through sheath 22. Moreover, the length of spines 14a/b can be altered so that collapsing forces and radial forces can be further reduced. For example, elongating spines 14a/b may reduce the forces needed to collapse device 10 and reduce radial forces.

When device 10 is in the collapsed configuration, it may be suited for being delivered via a suitable catheter or delivery sheath 22 as shown in FIG. 2. For example, it may be desirable to collapse device 10 and dispose it within sheath 22. Then, sheath 22 and device 10 can be advanced to the desired position and sheath 22 can be proximally retracted so that device 10 emerges therefrom and can shift to the expanded configuration. Alternatively, device 10 can be delivered by first positioning sheath 22 at the desired location and then advancing device 10 through sheath 22. Removal of device 10 may be accomplished in a number of different ways. For example, device 10 may be removed by simply retracting it proximally from the vasculature. Alternatively, device 10 may be retracted into or otherwise disposed in a suitable retrieval sheath or catheter.

In some embodiments, catheter or sheath 22 may be a microcatheter. The dimensions and general configuration of the microcatheter can vary. For example, catheter 22 may have an inside lumen diameter of about 0.016 to about 0.022 inches, or more or less. These dimensions may allow sheath 22 to be suitably sized to access a number of different vascular targets while having a lumen sized sufficient to allow device 10 to advance through or otherwise be disposed therein. In addition or in the alternative, sheath 22 may include a distal housing section configured for having basket region 16 (or other portions of device 10) disposed therein. Of course, a number of other delivery devices may be used including essentially any suitable structure.

A perspective view of device 10 is shown in FIG. 3. Here it can be seen that basket region 16 may include a plurality of loop structures 24 extending between spines 14*a/b*. The number, arrangement, and configuration of loops 24 may vary. For example, basket region 16 may include two or more, three or more, four or more, five or more, and so forth sets of loops 24. Each set may include a single loop 24, a pair of opposing loops 24 as shown in FIG. 3, or it may include three or more loops 24 disposed in essentially any suitable pattern or arrangement. Some of examples of other suitable arrangements and variations are described in more detail below.

As described above, device 10 may be configured so that basket region 16 is self-expanding. Alternatively, basket region 16 may be expanded in other ways. For example, basket region 16 may be expanded by longitudinally shifting a spine (e.g., spine 14*a*) by pushing or pulling on shaft 18. In some embodiments, a second shaft 27 may be attached adjacent the distal end of basket region 16, for example at the distal end of spine 14*b*, and extend proximally. This second shaft 27 may allow a clinician to manipulate both of spines 14*a/b* independently of one another by actuating either or both of shafts 18/27. It can be appreciated that any of the embodiments shown herein may include a shaft similar to shaft 27 if desired for collapsing and expanding the device or it's basket region.

The manufacturing of device 10 may include a number of different methods and techniques. For example, device 10 may be manufactured by laser-cutting, laser etching, chemical etching, or photo-chemical etching a tubular structure so as to define spines 14*a/b* and basket region 16. In some embodiments, basket region 16 and spines 14*a/b* can be defined by laser-cutting a tubular structure such as a hypodermic tube (i.e., a "hypotube"). This manufacturing method may be desirable for a number of reasons. For example, this method may allow spines 14*a/b* and basket region 16 to be formed in a relatively simple manner, with relatively few manufacturing steps. Additionally, following this method may allow shaft 18 to be defined by the proximal region of the hypotube. Accordingly, the manufacturing method may be further simplified by not requiring any welding or attaching steps to connect various structures of device 10. In addition, forming device 10 from a tubular structure may allow device to be passed over a guidewire or other guiding structure.

Alternatively, device 10 may be manufactured by cutting or forming the appropriate structures in a generally planar sheet of material and then, if necessary, attaching the ends of the planar structure or attaching one or more planar structures together in any suitable manner. For example, FIG. 3 shows an attachment point or weld line 26 in phantom line where the opposing sides of a sheet of material may be attached or welded. In addition to being a weld, attachment point 26 may include and suitable attachment such as an adhesive, a polymer strip, a thermal bond, a mechanical connection, etc.

It can be appreciated that most of the Figures depicting some of the embodiments of suitable clot pulling devices generally depict the basket region 16 as being at the distal end of device 10. However, this need not be the case. For example, some embodiments may include a basket region 16 that is generally disposed a distance proximal of the distal end of device 10. A number of different manufacturing methods may be employed in order to build such a device. For example, basket region 16 may be laser cut (or cut in any suitable manner) into device 10 at the desired position of a tubular structure such as a hypotube. Alternatively, basket region 16 may be made in a suitable way (such as by cutting a hypotube, forming a braid or helix having the desired structure, etc.) and then be attached to shafts or tubular structures on opposite ends thereof. Regardless of how this type of device is manufactured, it may still be possible to shift basket region 16 between the collapsed and expanded configurations in a manner similar to what is described herein. For example, basket region 16 may be made from a shape memory material or otherwise be self-expanding. Alternatively, one or more shafts (e.g., shaft 18/27) may be attached adjacent the proximal and distal ends of basket region 16 so that spines 14*a/b* can be moved and so that basket region 16 can be expanded and collapsed.

As described above, all or portions of device 10 may be manufactured from materials such as nickel titanium alloy. However, any suitable material may be used including metals, metal alloys, polymers, etc. Some examples of suitable metals and metal alloys include stainless steel, such as 304V, 304L, and 316L stainless steel; linear-elastic or super-elastic nitinol or other nickel-titanium alloys, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material.

Some examples of suitable polymers may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example a polyetherester elastomer such as ARNITEL® available from DSM Engineering Plastics), polyester (for example a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), silicones, polyethylene (PE), Marlex high-density polyethylene, Marlex low-density polyethylene, linear low density polyethylene (for example REXELL®), polyethylene terephthalate (PET), polyetheretherketone (PEEK), polyimide (PI), polyetherimide (PEI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments portions or all of device 10 can be blended with a liquid crystal polymer (LCP). For example, the mixture can contain up to about 5% LCP.

In some embodiments, a coating, for example a lubricious, a hydrophilic, a protective, or other type of coating may be applied over portions or all device 10. Hydrophobic coatings such as fluoropolymers provide a dry lubricity which improves device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In some embodiments, the sheath or coating may be applied over basket region 16. This may provide extra surface area to contain clots that might be captured therein.

The sheath or polymeric layer coating may be formed, for example, by coating, by extrusion, co-extrusion, interrupted layer co-extrusion (ILC), or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Device 10, or portions thereof, may also be coated, plated, wrapped or surrounded by, doped with, or otherwise include a radiopaque material. For example, spines 14*a/b* and/or basket region 16 may be made from a radiopaque material or may include a radiopaque marker member or coil coupled thereto. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, plastic material loaded with a radiopaque filler, and the like.

In some embodiments, a degree of MRI compatibility may be imparted into device 10. For example, to enhance compatibility with Magnetic Resonance Imaging (MRI) machines, it may be desirable to make portions of device 10, in a manner that would impart a degree of MRI compatibility. For example, device 10, or portions thereof, may be made of a material that does not substantially distort the image and create substantial artifacts (artifacts are gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, Elgiloy, MP35N, nitinol, and the like, and others.

A perspective view of device 10 in the collapsed (or nearly collapsed) configuration is shown in FIG. 4. Here it can be seen how spine 14*b* may extend distally beyond the distal end of spine 14*a* when basket region 16 is collapsed. It can also be seen that as basket region 16 is collapsed, its structure begins to resemble that of a tube, for example, a hypotube from which device 10 has been manufactured from.

As seen in FIGS. 1-4, both the proximal and distal ends of basket region 16 may be generally "open" so that a clot can captured by passing the clot into either end of basket region 16. It is not necessary, however, to have both ends of basket region 16 open. For example, FIG. 5 illustrates device 110 that is similar to device 10 except that device 110 includes an end loop 128 that "closes" one of the ends of basket region 116 (in this case the distal end of basket 116). This configuration may be desirable by allowing device 110 to capture a clot within basket region 116 while decreasing the possibility that the clot will pass out of the other end of basket region 116. Accordingly, basket region 116 may include both loops 124 and end loop 128 that, collectively, define basket region 116 that has a somewhat cylindrical or conical shape.

In general, end loop 128 may extend between spines 114*a/b* and may be slightly curved in order to allow shifting of the position of spines 114*a/b* in a manner similar to what is described above. Although end loop 128 is depicted in FIG. 5 to be at the distal end of basket region 116, this need not be the case. For example, end loop 128 may be positioned near the proximal end of basket region 116 (i.e., adjacent shaft 118).

FIG. 6 illustrates device 210 that is similar to devices 10 and 110 except that device 210 includes side rails or spines 230*a/b* and loops 224*a/b/c*/d/e that are spaced are various distances. Accordingly, a number of features attributable to this and other embodiments can be seen. For example, by including side rails 230*a/b*, which may be or resemble spines 214*a/b*, it can be seen that the number of spines may vary from two, three, four or more. Additionally, basket 216 (as well as other basket regions described herein) may includes loops 224*a/b/c*/d/e that vary number, shape, and configuration. For example, FIG. 6 illustrates that device 10 may include five sets of loops 224*a/b/c*/d/e. However, any suitable number of loops 224*a/b/c*/d/e may included including two, three, four, five, six, or more.

It can also be seen in FIG. 6 that the pattern or arrangement of loops 224*a/b/c/d/e* may vary. For example, the distance between loop 224*a* and loop 224*b* may vary greatly and could be about 0.008 to about 0.020 inches or more or less. The spacing between loop 224*b* and loop 224*c* (as well as between loop 224*c* and loop 224*d*, and between loop 224*d* and loop 224*e*) may be different from the previously mentioned spacing. The overall length of basket region 216 may also vary. For example, basket region may have a length in the range of about 1 to about 15 millimeters or more or less.

Device 210 can be made and used similar to what is described above. For example, device 210 may be delivered using a suitable delivery device (e.g., sheath 22). Basket region 216 may be configured to shift between the collapsed and expanded configuration in essentially any of the ways described above. For example, basket region 216 may be self-expanding or it may be expandable by actuating shaft 218.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for removing clots from a blood vessel, comprising the steps of:
    providing a clot pulling device including a first spine having a proximal end, a second spine disposed parallel to the first spine, a pushing member coupled to the proximal end of the first spine and extending proximally therefrom, and a basket disposed between and coupled to the first and second spines;
    providing a catheter having a lumen extending therethrough;
    advancing the catheter through a blood vessel to a location adjacent an area of interest;
    advancing the clot pulling device through the lumen of the catheter to a position distally of the area of interest;
    expanding the basket;
    entrapping a clot within the basket;
    advancing the catheter through a blood vessel to a location adjacent an area of interest includes disposing the clot pulling device in the lumen and advancing the catheter and the clot pulling device through the blood vessel; and
    advancing the clot pulling device through the lumen of the catheter to a position distally of the area of interest includes pushing the clot pulling device in the distal direction with the pushing member.

2. The method of claim 1, wherein the step of advancing the clot pulling device through the lumen of the catheter to a position distally of the area of interest includes advancing the clot pulling device out from a distal end of the catheter.

3. The method of claim 1, wherein the step of expanding the basket includes applying force in the distal direction to the pushing member.

* * * * *